United States Patent
Klein

(10) Patent No.: US 7,842,095 B2
(45) Date of Patent: Nov. 30, 2010

(54) ANTIBIOTIC BONE CEMENT SPACER

(75) Inventor: Robert W. Klein, Chestnut Ridge, NY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 323 days.

(21) Appl. No.: 11/900,628

(22) Filed: Sep. 11, 2007

(65) Prior Publication Data

US 2009/0069899 A1 Mar. 12, 2009

(51) Int. Cl.
A61F 2/30 (2006.01)
A61B 17/56 (2006.01)

(52) U.S. Cl. .............. 623/23.19; 623/22.4; 623/23.52; 606/94

(58) Field of Classification Search ............... 623/22.4, 623/23.11, 23.19, 23.44, 23.45, 23.46, 23.52; 606/94
See application file for complete search history.

(56) References Cited

U.S. PATENT DOCUMENTS

| | | | |
|---|---|---|---|
| 3,882,858 | A | 5/1975 | Klemm et al. |
| 4,283,799 | A | 8/1981 | Pratt, Jr. et al. |
| 4,919,666 | A | 4/1990 | Buchhorn et al. |
| 5,123,927 | A | 6/1992 | Duncan et al. |
| 5,133,771 | A | 7/1992 | Duncan et al. |
| 5,538,514 | A | 7/1996 | Hawkins |
| 5,593,446 | A * | 1/1997 | Kuoni .................. 623/23.44 |
| 5,618,286 | A | 4/1997 | Brinker |
| 5,665,121 | A | 9/1997 | Gie et al. |
| 5,827,289 | A | 10/1998 | Reiley et al. |
| 5,980,573 | A | 11/1999 | Shaffner |
| 6,155,812 | A | 12/2000 | Smith et al. |
| 6,214,053 | B1 | 4/2001 | Ling et al. |
| 6,241,772 | B1 * | 6/2001 | Mackwood Ling et al. ...... 623/23.15 |
| 6,245,111 | B1 | 6/2001 | Shaffner |

(Continued)

FOREIGN PATENT DOCUMENTS

WO 00/03855 1/2000

OTHER PUBLICATIONS

Younger et al., The Outcome of Two-stage Arthroplasty Using a Custom-made Interval Spacer to Treat the Infected Hip, The Journal of Arthroplasty, vol. 12, No. 6, pp. 615-623, 1997.

(Continued)

Primary Examiner—Bruce E Snow
Assistant Examiner—Melissa Hoban
(74) Attorney, Agent, or Firm—Lerner, David, Littenberg, Krumholz & Mentlik, LLP

(57) ABSTRACT

A temporary femoral implant system has a porous mold and a femoral component. The system fits at least partially in a femoral cavity. The mold has a wall with an interior surface and an exterior surface forming an interior space for receiving an antibiotic bone cement. The mold allows the antibiotic to diffuse through the wall to the exterior surface. The femoral component has a stem portion received within the mold. A method of using the implant system includes providing an implant system comprising a mold and a femoral component, inserting the mold into the femoral cavity with the exterior surface facing the femoral cavity, inserting the stem portion of a femoral component into the interior space of the mold and filling the interior space of the mold with an antibiotic bone cement.

26 Claims, 8 Drawing Sheets

U.S. PATENT DOCUMENTS

| | | | |
|---|---|---|---|
| 6,299,448 B1 * | 10/2001 | Zdrahala et al. | 433/173 |
| 6,361,731 B1 | 3/2002 | Smith et al. | |
| 6,942,475 B2 | 9/2005 | Ensign et al. | |
| 2001/0051831 A1 * | 12/2001 | Subba Rao et al. | 623/22.42 |
| 2004/0098134 A1 * | 5/2004 | Meulink | 623/23.52 |
| 2005/0021150 A1 | 1/2005 | Michelson | |
| 2005/0085918 A1 | 4/2005 | Soffiati et al. | |
| 2005/0107885 A1 | 5/2005 | Evans | |
| 2005/0119756 A1 | 6/2005 | Soffiati et al. | |
| 2005/0131269 A1 | 6/2005 | Talmadge | |

OTHER PUBLICATIONS

Deshmukh et al., An Intramedullary Cement Spacer in Total Hip Arthrplasty, The Journal of Arthroplasty, vol. 13, No. 2, pp. 197-199, 1998.

Zilkens et al., Treatment of an old infection in a total hip replacement with an interim spacer prosthesis, Arch. Orthop. Trauma Surg., No. 109, pp. 94-96, 1990.

W. Abendschein, Salvage of Infected Total Hip Replacement: Use of Antibiotic/PMMA Spacer, Acta Orthop Scand, vol. 65, No. 1, pp. 7-8, 1994.

Duncan et al., The Antibiotic Loaded Hip Replacement. A Valuable Tool in the Management of the Complex Infected THA, J Bone Joint Surg., vol. 73-B, Supp II, (pages unknown), 1991.

Duncan et al., A Temporary Antibiotic Loaded Joint Replacement System for Management of Complex Infections Involving the Hip, Orthopedic Clinics of America, vol. 24, No. 4, pp. 751-759, Oct. 1993.

Duncan et al., The Role of Antibiotic-Loaded Cement in the Treatment of an Infection after a Hip Replacement, The Journal of Bone and Joint Surgery, vol. 76-A, No. 11, pp. 1742-1751, Nov. 1994.

Kraay et al., Use of an Antibiotic Impregnated Polymethyl Methacrylate Intramedullary Spacer for Complicated Revision Total Hip Arthroplasty, The Journal of Arthroplasty, vol. 7, Supp. 1992, pp. 397-402, 1992.

Hofmann et al., Ten-Year Experience Using Articulating Antibiotic Cement Hip Spacer for the Treatment of Chronically Infected Total Hip, The Journal of Arthroplasty, vol. 20, No. 7, pp. 874-879, 2005.

Leunig et al., A Cement Spacer for Two-Stage Revision of Infected Implants of the Hip Joint, International Orthopaedics, (SICOT), No. 22, pp. 209-214, 1998.

Krackow et al., Preservation of Fascial Planes and Soft Tissue Tension in Revision Joint Surgery, Orthopedics, vol. 11, No. 5, pp. 803-806, May 1998.

Oxborrow et al., New Uses for Gentaminicin-Impregnated Polynethyl Methacrylate Spacers in Two-Stage Revision Hip Arthroplasty, The Journal of Arthroplasty, vol. 12, No. 6, pp. 709-710, 1997.

Ries et al., An Inexpensive Molding Method for Antibiotic-Impregnated Cement Spacers in Infected Total Hip Arthroplasty, The Journal of Arthroplasty, vol. 14, No. 6, pp. 764-765, 1999.

Kendall et al., Temporary Antibiotic Loaded Acrylic Hip Replacement: A Novel Method for Management of the Infected THA, Seminars in Arthroplasty, vol. 5, No. 4, pp. 171-177, Oct. 1994.

Magnan et al., Performed Acrylic Bone Cement Spacer Loaded With Antibiotics, Acta Orthop Scand, vol. 72, No. 6, pp. 591-594, 2001.

Backgrounds of Antibiotic-Loaded Bone Cement and Prosthesis-Related Infection, Chapter 1, Biomaterials, pp. 3-23, 2003.

http://naplestotaljoint.corn, BTJC, Bertram Total Joint Centers, Hip Spacer for Infection of Total Hip, Nov. 2002.

Alexeeff et al., Structural Allograft in Two-Stage Revisions for Failed Septic Hip Arthroplasty, The Journal of Bone and Joint Surgery, vol. 78-B, No. 2, pp. 213-216, Mar. 1996.

Cohen et al., Two-Stage Reimplantation of Septic Total Knee Arthroplasty, The Journal of Arthroplasty, vol. 3, No. 4, pp. 369-377, Dec. 1998.

Booth et al., The Results of Spacer Block Technique in Revision of Infected Total Knee Arthroplasty, Clinical Orthopaedics and Related Research, No. 248, pp. 57-60, Nov. 1989.

Goldstein et al., Temporary Articulating Methylmethacrylate Antibiotic Spacer (TAMMAS), The Journal of Bone and Joint Surgery, vol. 83-A, Supp. 2, Part 2, pp. 92-97, 2001.

Prostalac Hip, Short-term Total Hip Replacement, Surgical Technique, De Puy, pp. 1-10, 2003.

The Bertram Spacer, www. surgicaltechnique.net, product information, 2002.

Ivarsson et al., Revision of infected hip replacement, Acta Orthop Scand, vol. 65, No. 1, pp. 7-8, 1994.

Evans et al., Successful Treatment of Total Hip and Knee Infection with Articulating Antibiotic Components, Clinical Orthopaedics and Related Research, No. 427, pp. 37-46, 2004.

Antibiotic-Loaded Bone Cement in Aseptic Total Joint Replacemetn: Whys, Wherefores and Caveats, AAOS, 72nd annual meeting, Washington, DC, Feb. 23-27, 2005.

Introducing Cemex, Cemex Isoplastic, Cemex RX, Cemex XL, Tecres S.p.A., 1998.

* cited by examiner

ANTIBIOTIC BONE CEMENT SPACER

BACKGROUND OF THE INVENTION

The present invention relates to a temporary femoral implant and a method of implanting a temporary femoral implant.

Total joint replacement may result in infection. One technique to help address this problem involves a surgical procedure referred to as a two-stage joint replacement revision procedure. In the first stage of this procedure for a hip replacement, the existing hip replacement (prosthesis) and infected tissue are removed from the femoral and acetabular cavities. Antibiotic bone cement along with a temporary implant (also called a spacer) is placed in the femoral and acetabular cavities and left there for a period of time until the infection has been reduced to an acceptable level. Once such time has elapsed, in the second stage of the procedure, the bone cement is removed and a new hip replacement is implanted into the femoral and acetabular cavities in a well-known manner. U.S. Pat. No. 5,133,771 relates to a custom femoral implant using a latex envelope as a mold for bone cement. The cement-filled mold cures in the femoral cavity and the mold and cement removed; the latex discarded, and the cement reimplanted.

U.S. Pat. Nos. 5,980,573 and 6,155,812 relate to temporary antibiotic bone cement implants used in a two-stage joint replacement.

SUMMARY OF THE INVENTION

The present invention relates to a temporary femoral component implant for implanting in the femoral cavity. The temporary implant includes a femoral component pre-assembled to or supplied with a flexible mold which is inserted into a femoral cavity and filled with a cement composition comprising uncured bone cement and an antibiotic, wherein the mold is adapted to allow the antibiotic to diffuse to the exterior surface. Such a bone cement is Simplex™ P with Tobramycin supplied by Stryker Corp. The cement is supplied through an opening in the temporary stem. The resultant implant comprises the femoral component surrounded by cured antibiotic loaded bone cement in the shape of the interior space of cavity with the mold remaining on the outer surface of the cured cement. The flexibility of the mold allows the surrounding bone or the surgeon to influence the final shape of the implant without directly contacting the cement.

One aspect of the present application is a temporary femoral component implant system for implanting in the femoral cavity. The temporary implant system includes a flexible fabric mold and a femoral component. The mold is adapted to fit at least partially in a femoral cavity. The mold has an interior surface and an exterior surface forming an interior space. The interior space is adapted to support a cement composition comprising uncured bone cement and an antibiotic, wherein the mold is adapted to allow the antibiotic to diffuse to the exterior surface but prevent bone cement from contacting bone. The femoral component has a stem portion adapted to fit at least partially in the interior space of the mold.

Another aspect of the present application is a method of implanting a temporary femoral component implant in the femoral cavity. The method includes providing an implant comprising a mold and a femoral component, inserting at least a portion of the implant into the femoral cavity with the exterior surface facing the femoral cavity, inserting at least a portion of the stem portion of a femoral component into the interior space of the mold and filling at least a portion of the interior space of the mold with an antibiotic cement composition.

As used herein when referring to bones or other parts of the body, the term "proximal" means close to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body.

DETAILED DESCRIPTION OF THE INVENTION

Figure 1:
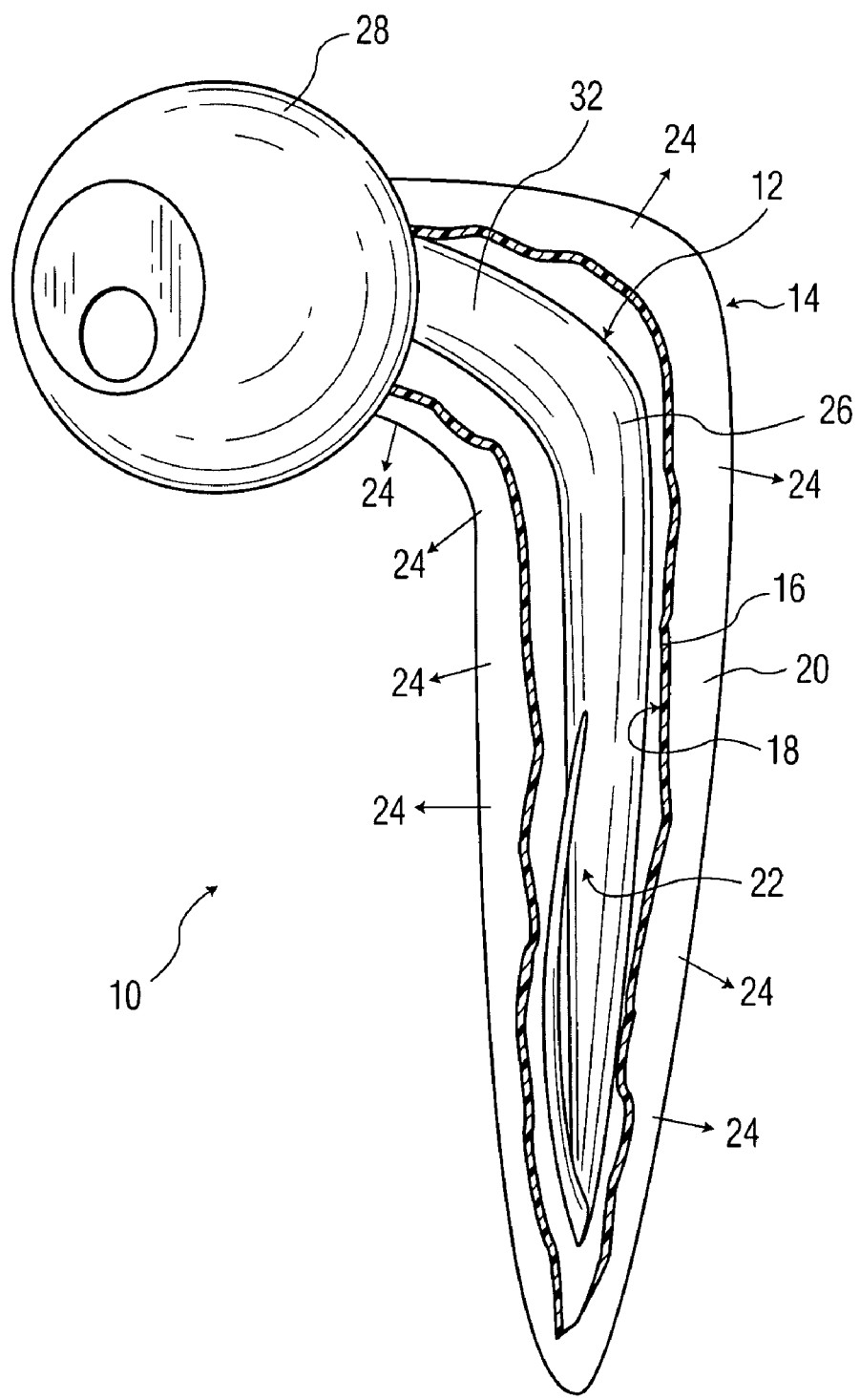
FIG. 1 is an anterior view of temporary implant system of the present invention showing the left femoral component and a partial cutaway of a mold.
Figure 2:
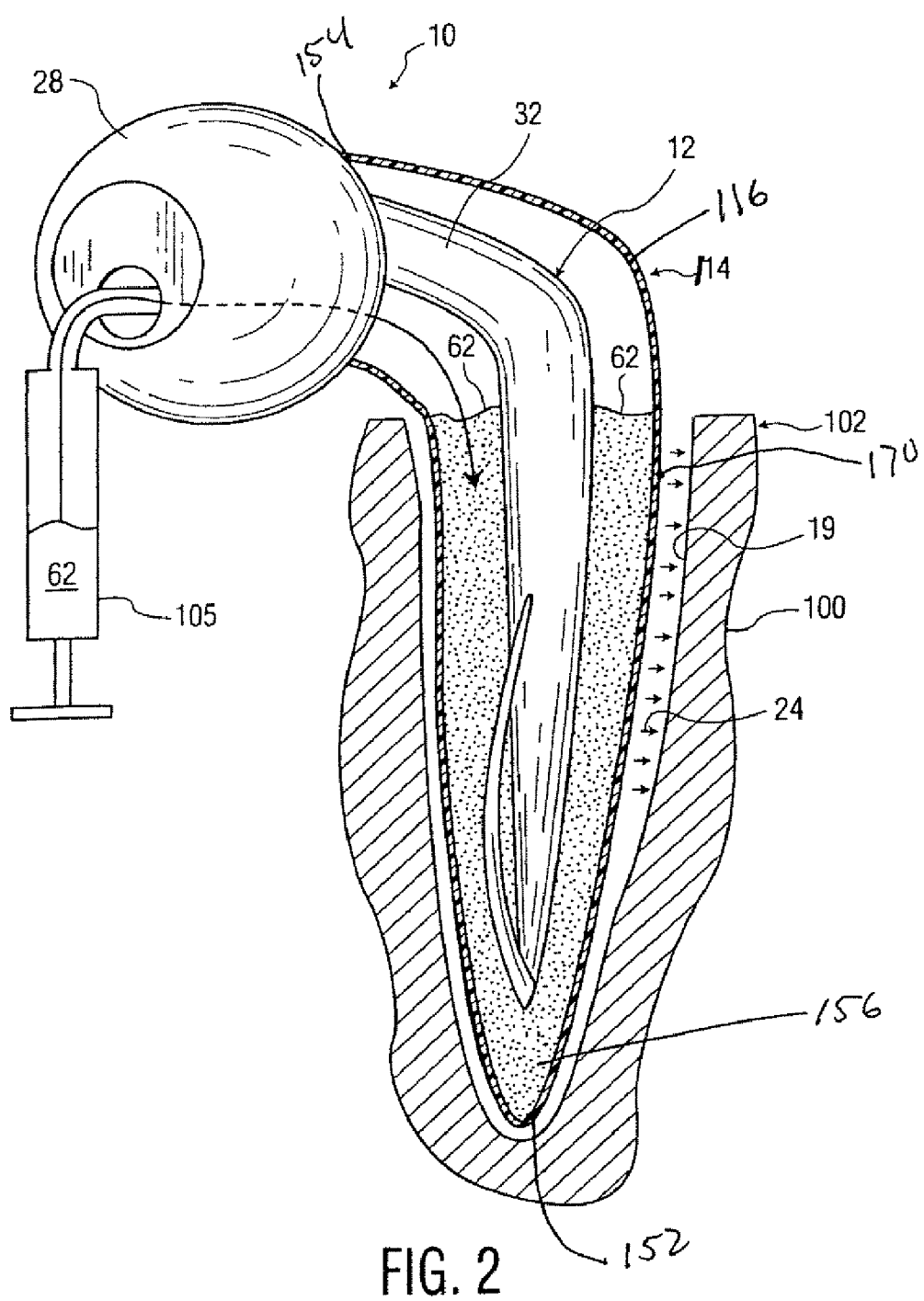
FIG. 2 is a partial cutaway, anterior view of a left femoral cavity with the left femoral component implant of FIG. 1 implanted therein, including a syringe for introducing the antibiotic bone cement.

FIG. 1 shows a partial cutaway, anterior view of a left temporary femoral implant system 10 according to an embodiment of the present invention. Obviously, a similar implant can be used on the right femur. The femoral implant system 10 comprises a femoral component 12 detachably connected to a mold 14 to form a pre-assembled unit. As shown in FIG. 2, the implant system 10 can be part of a temporary femoral implant kit for use in a surgical procedure such as for implantation into a femoral cavity 19 as part of a surgical procedure referred to as a two-stage hip replacement revision procedure. The femoral implant kit may also include a bone cement composition 62 which can be used to fill the interior of mold 14. The mold 14 is shown as a flexible liner adapted to fit at least partially in femoral cavity 19. The mold 14 includes a wall 16 with an interior surface 18 and exterior surface 20 wherein the wall forms an interior space adapted to support a bone cement composition such as, initially, an uncured bone cement and an antibiotic. Mold 14 is adapted to allow the antibiotic to diffuse, as shown by arrows 24, from interior surface 18 and to exterior surface 20 and to femoral cavity 19 but inhibit the uncured bone cement from diffusing through wall 16 to exterior surface 20. As seen in FIG. 1, the femoral component 12 is shown as an elongated body 26 adapted to fit at least partially in the interior space 22 of the mold. A head portion 28 is adjustably attached to a proximal neck portion 32 of stem 26. The head 28 has a generally spherical shape sized to fit into an acetabular cavity (not shown). As explained below, the implant system 10 can be implanted into a femoral cavity as a completed pre-assembled unit without having to remove mold 14 from femoral component 12. In this manner, implant system 10 allows the surgeon and/or surrounding bone to influence the shape of the uncured bone cement without the bone contacting the uncured bone cement. In addition, the implant 10 allows the antibiotic to diffuse out of the cured bone cement, through mold 14, and into femoral cavity 19 to help reduce or eliminate infection therein during the first stage of a two-stage hip replacement revision procedure.

FIGS. 3-6 show femoral component 12 of femoral implant system 10 of FIG. 1 in further detail. The elongated body 26 has a proximal neck portion 34 and a distal stem portion 36 with a distal tip 30 adjacent to and at an angle to the neck portion 34. Stem portion 36 is adapted to fit into the interior of the mold 14 and into a femoral cavity and a proximal end 32 of neck portion 34 adjustably receives head portion 28. The dimensions of the head portion, such as the diameter of the head portion, can be selected depending on size of the acetabular cavity or other requirements, as the case may be. Multiple head portions can be supplied for this purpose. The preferred body 26 is a bent rod or shaft with a rounded portion 36a located at the distal tip 30 and a medial arm 36b extending from the rounded portion toward the proximal end 32. The medial arm 36b is attached to the distal end, spaced apart by a distance 36c and made of a flexible material to provide a snug fit when the body 26 is inserted into the femoral cavity. The body 26 can be made of a bio-compatible material such as a stainless steel, titanium, titanium alloy, cobalt-chrome, or the like.

Figure 3:
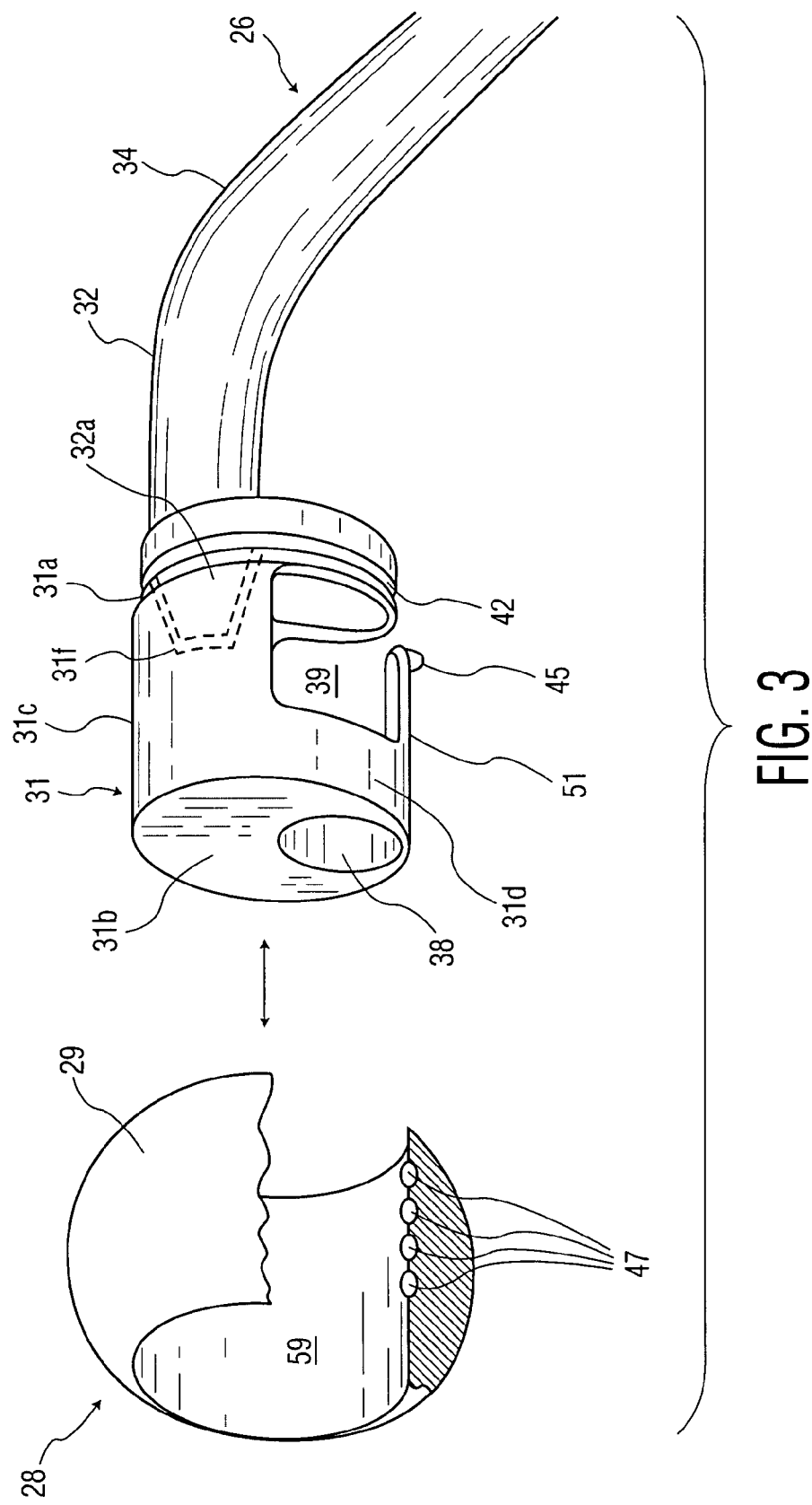
FIG. 3 is an exploded view of the femoral component of FIG. 1 showing the head removed from the stem.
Figure 4:
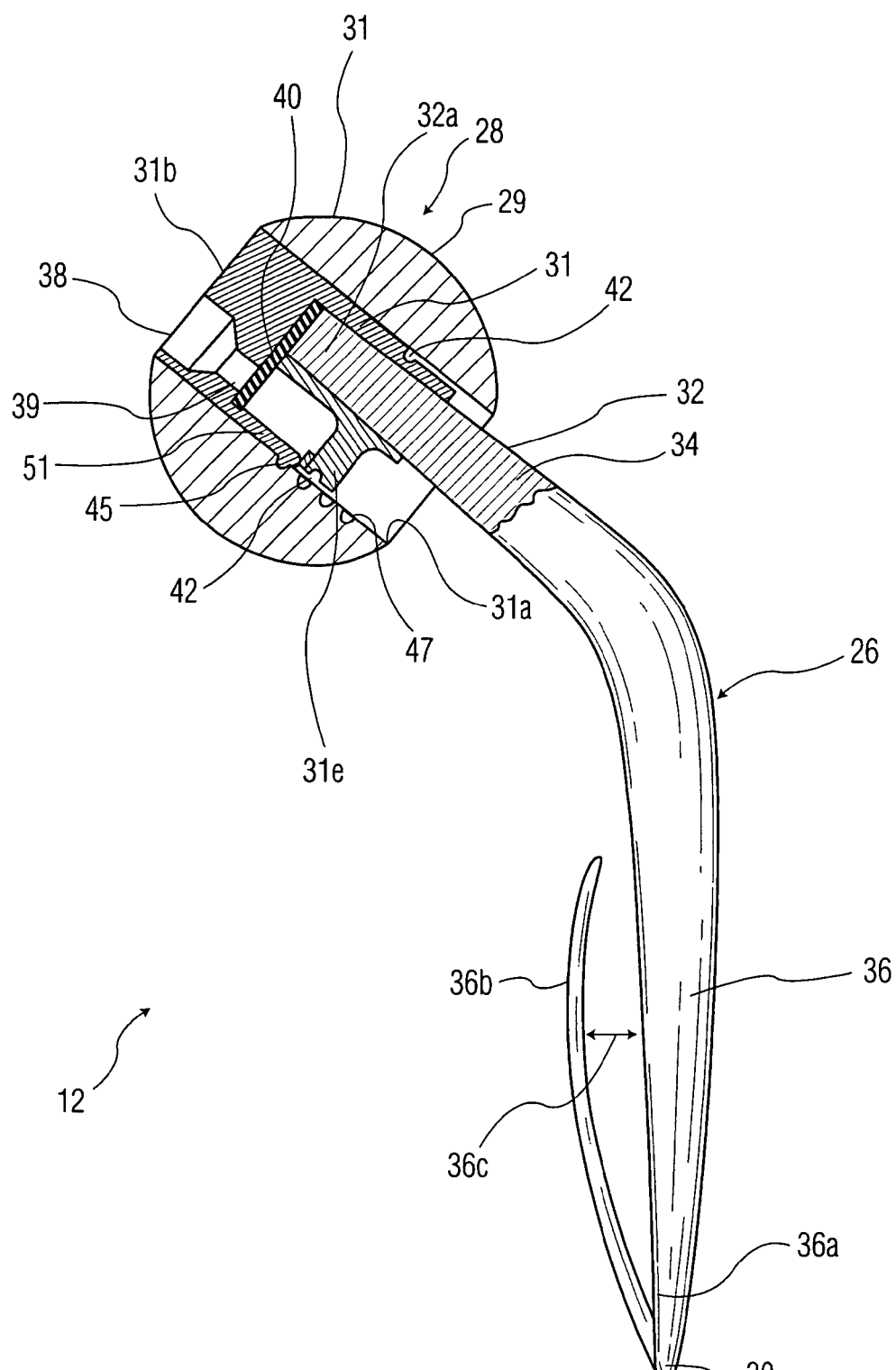
FIG. 4 is an anterior view of the proximal femoral component, including the head, of FIG. 1, with the proximal stem and head in cross-section.
Figure 5:
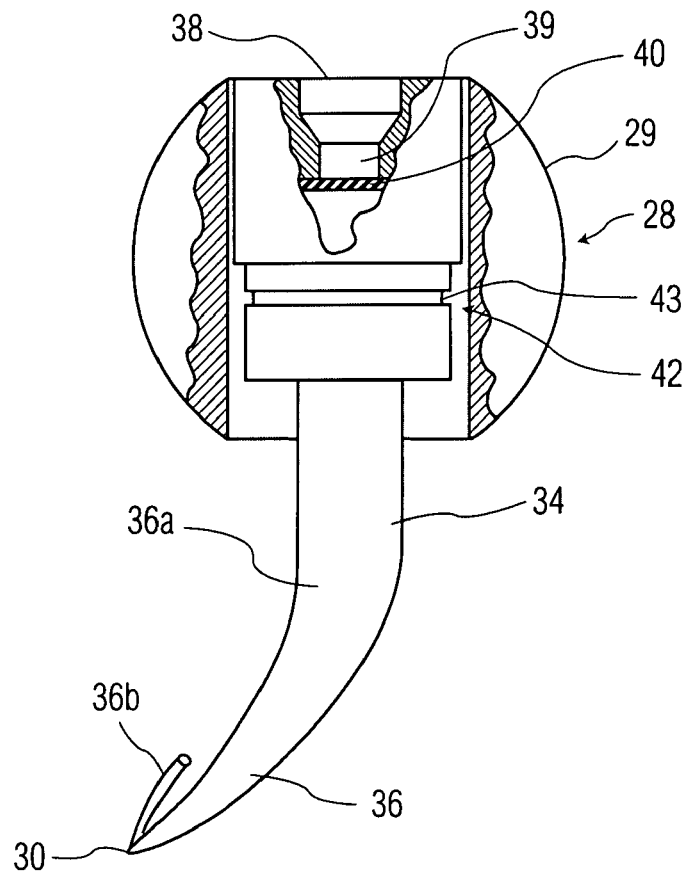
FIG. 5 is a top view of the head, proximal, and distal portions of the femoral component of FIG. 1 with the head partially cut away.

In the preferred embodiment, head portion 28 comprises a two part assembly comprising a part-spherical first component 29 and a second component 31 (see FIG. 3). As explained below in detail, the first component 29 is adjustably coupled to the second component 31 to adjust the length of the femoral body. The head portion 28 can be made of a bio-compatible material such as metal or preformed PMMA (polymethyl methacrylate with or without antibiotic) polyethylene.

The second component 31 has a partial generally cylindrical outer surface 31c and a proximal flat surface 31b. The preferred portion 31 includes a female tapered base 31f designed to receive a conical trunion 32a of proximal stem portion 32. The tapers may be the well-known Morse tapers used extensively in orthopedic implant design includes an injection port 38 in top surface 31b to allow a material, such as a bone cement composition 62, to be injected into the interior space of the mold 14 after the system 10 has been inserted. The injection port 38 includes an opening on the surface 31b of the second component 31 through a flange 31d and into a channel 39 extending through flange 31e of bottom surface 31a of the proximal stem portion. Located below flange 31d within the channel 39 is a check valve 40, best seen in FIG. 4, adapted to prevent material such as cement composition 62 which was injected into the injection port 38 from flowing back out through the injection port. In one embodiment, the check valve is a rubber flap attached at one end to the bottom surface of flange 31d configured to prevent or reduce the flow of cement out of the injection port while the uncured bone cement composition is curing or hardening.

When the protrusion 45 is placed in the most distal indentation 47, a cavity 59 is created in head 28 by the central bore therein. This cavity can be filled with bone cement flush with the top of head 28.

Figure 6:
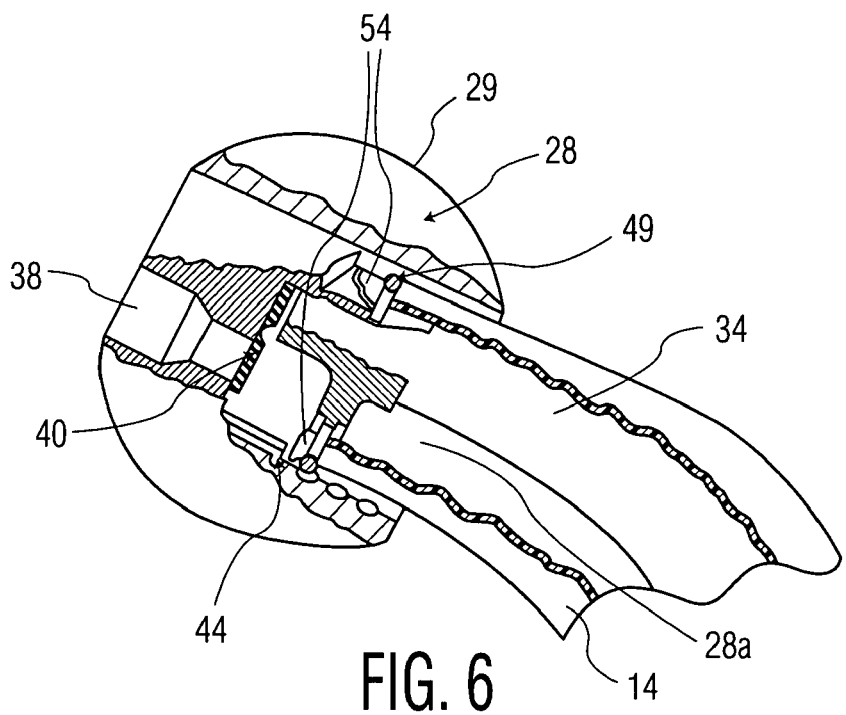
FIG. 6 is a cutaway view of the proximal portion of the femoral component stem and head of FIG. 1.

Located near the distal end 31a of the second component and above flange 31e is an attachment mechanism in the form of groove 42 adapted to detachably couple the open, proximal end of mold 14 to the distal end 31a of the second component. In the preferred embodiment, attachment groove 42 receives a split ring 49, as best seen in FIG. 6, configured to mechanically clamp a proximal open end 54 of mold 14 into groove 42 above flange 31e. The second component 31 of implant system 10 is later coupled to the part-spherical portion 29 of head portion 28.

The head 28 includes an adjustment system adapted to set the axial relationship of first component 29 to second component 31 to allow adjustment of the length and head offset of the femoral implant system. In a preferred embodiment, the adjustment mechanism comprises a semi-spherical protrusion 45 coupled to a deflectable member 51 mounted on or integral with second head portion 31. Protrusion 45 interfaces with corresponding part-spherical indentations 47 in first component 29. The indentations 47 are spaced to allow fixed increments of neck length adjustment to aid in soft tissue tensioning, for example, at two millimeters. Additional, adjacent indentations allow the cement material to mechanically lock the head in position once the cement has hardened.

Figure 7:
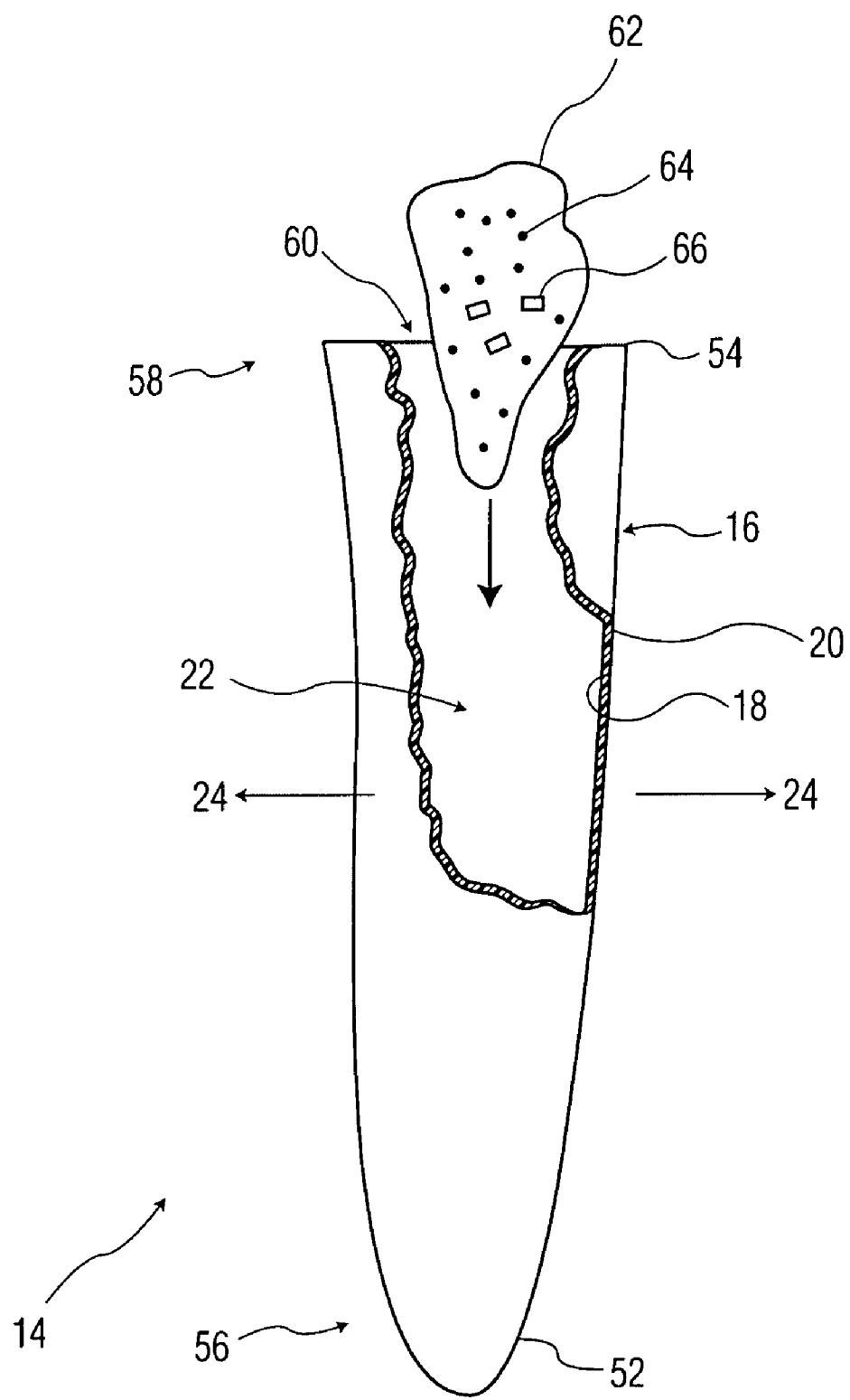
FIG. 7 is an elevation view of the mold of FIG. 1.

Referring to FIG. 7, there is shown an anterior, partial cutaway view of mold 14 of FIG. 1. The mold 14 is a generally flexible liner defined by a wall 16 having a closed end portion 52 at its distal end 56 and an open end portion 54 at its proximal end 58. Mold 14 has a tapered shape with a relatively wide proximal end 58 tapering inward from proximal end 58 to distal end 56. Wall 16 defines an interior space 22 to accommodate a bone cement composition 62 such as an antibiotic bone cement. As the uncured bone cement 62 hardens (cures or sets), mold 14 forms a final shape based on various factors including, but not limited to, volume of cement composition added, mold shape, surrounding bone shape, and surgeon contouring. The bone cement 66 can include Simplex™ P brand bone cement with Tobramycin manufactured by Stryker Corp. The Tobramycin reduces infection by killing the bacteria causing the infection. The bone cement composition 62 can be introduced into the interior space 22 through an opening 60 located at the open end portion 54 of mold 14. The interior surface 18 and the exterior surface 20 of wall 16 are porous to allow the antibiotic 64 to diffuse outward from the interior 22 and through wall 16 (shown by arrows 24) but substantially prevent or inhibit the diffusion of monomers and polymers of the uncured bone cement 66 through the exterior surface.

Figure 8:
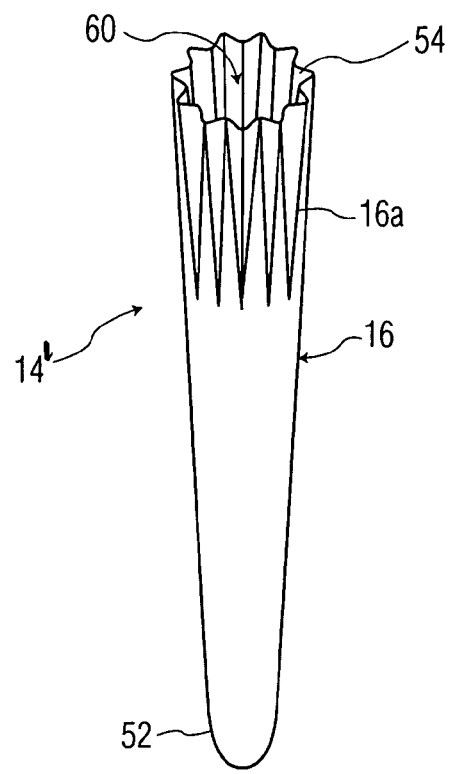
FIG. 8 is an isometric view of an expandable mold similar to the mold of FIG. 7 showing the expandable mold in a collapsed condition.
Figure 9:
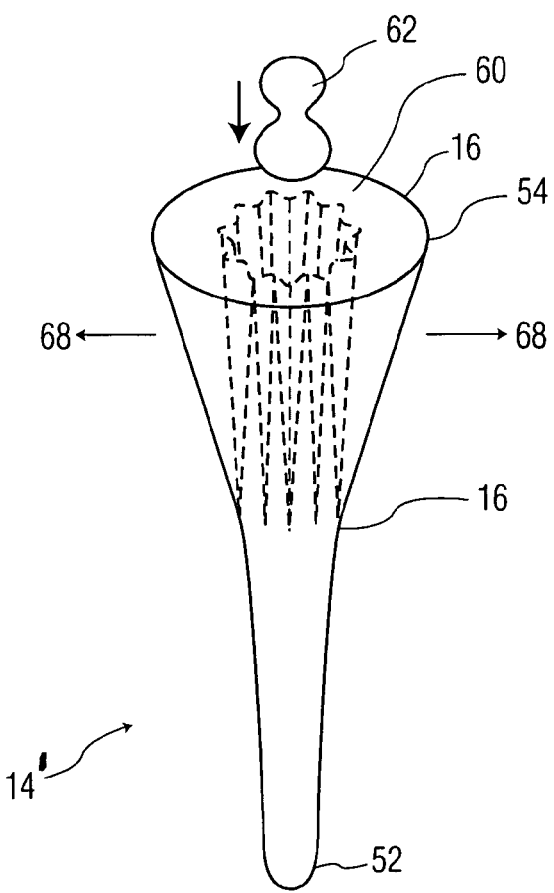
FIG. 9 is an isometric view of the mold of FIG. 8 showing the mold in an expanded condition.

Referring to FIG. 8, there is shown a lateral view of an expandable mold 14 in a non-expanded condition, and FIG. 9 shows an isometric view of mold 14' in an expanded condition. The non-expanded or collapsed condition occurs when the mold is empty or not filled with a bone cement composition. The mold 14' is made of a pleated, or wrinkled flexible material 16a that allows it to expand to accommodate a material such as a bone cement composition 62 inserted in its interior space. The expanded condition refers to when the mold 14' is filled, at least partially, with the bone cement composition and the mold expands to accommodate the composition. This occurs when the end 54 is attached to groove 42 of component 31. Referring to FIG. 9, the mold 14' is shown as having a relatively small diameter in the non-expanded condition before the bone cement composition is introduced into the interior space of the mold. Referring to FIG. 8, the mold is shown in the expanded condition after the bone cement composition 62 has been introduced into the interior space 22. The pleated wall 16 and interior space 22 expand outwardly to accommodate the bone cement, as shown by arrows 68.

Figure 10:
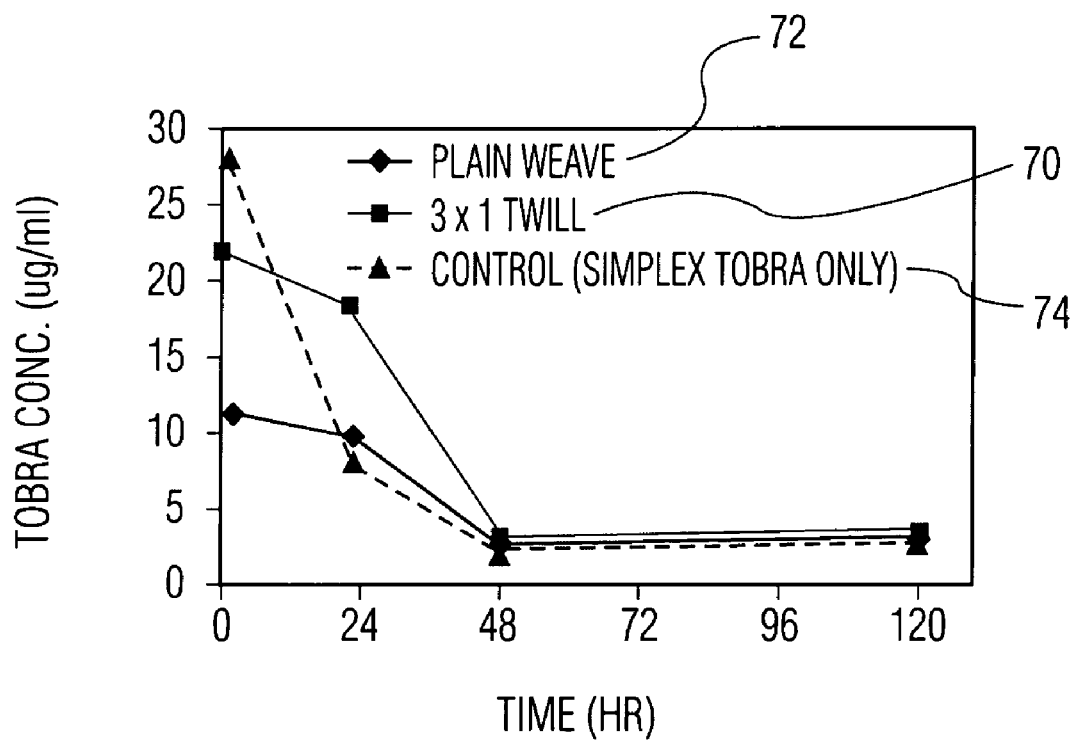
FIG. 10 is a chart showing comparative antibiotic release characteristics of the mold of FIG. 7.

Referring to FIG. 10, there is shown a chart showing the antibiotic release versus time comparative date of a mold 14 of FIG. 7 made from two different fabrics. The chart shows how the porous weave of mold 14 allows the diffusion of the antibiotic. These characteristics are controlled by various factors including, but not limited to, thread material and fabric weave. In a first embodiment, the mold 14 can be made of a polyester thread material used for vascular grafting or the like woven as a plain weave. In a second embodiment, mold 14 is made of the same polyester fabric with a weave comprising a 3×1 twill weave. Mold 14 of the present application with the twill is represented in the graph by arrow 70 compared to a mold having a plain weave represented by arrow 72. A control (antibiotic loaded cement that has been cured but without a mold) is represented by arrow 74. The control 74 results in a concentration of about 28 µg/ml of the antibiotic Tobramycin after about 1 hour in buffered saline. In the control condition 74, from about 1 hour to 24 hours, additional Tobramycin antibiotic has diffused to result in an increase in concentration of about 10 µg/ml and, from about 24 hours to 48 hours, additional Tobramycin antibiotic has diffused to result in an increase in concentration of about 2 µg/ml. Samples from the same batch of antibiotic loaded cement cured in the "plain weave" mold shown by arrow 72, had less antibiotic diffusion at about 1 and 24 hours than the control, and from 24 to 48 hours, Tobramycin antibiotic has diffused to result in an increase in concentration of about 2 µg/ml. In contrast, samples from the same batch of antibiotic loaded cement cured in the "twill weave" mold shown by arrow 70, resulted in 1 hour and 24 hour antibiotic concentrations of 22 µg/ml and 17 µg/ml and, after 48 hours, about 2 µg/ml. Thus, the "twill weave" mold of the present application, shown by arrow 70, exhibits relatively good diffusion characteristics.

FIG. 2 shows an elevational view of a mold 114 according to another embodiment of the present application. The mold 114 has various physical features similar to those of mold 14 of FIG. 1. For example, the mold 114 has a wall 116 and a closed end portion 152 at its distal end 156 and an open proximal end portion 154 connected to head 28. However, the exterior surface of the wall 116 is coated, at least partially, with an antibiotic 170, compared to the exterior surface of the mold 14 which has no such coating. The antibiotic 170 is adapted to diffuse from the exterior surface and into the infected areas of the interior of the femoral cavity 19. In contrast, in the mold 14, the antibiotic is only introduced in combination with the uncured cement into the interior of the mold then allowed to diffuse outward through the exterior surface. Of course mold 114 is also filled with antibiotic bone cement.

The surgical method for using the implant system 10 of the present invention is best understood by reference to FIGS. 2-6. FIG. 2 illustrates a portion of a surgical procedure using the temporary femoral implant system 10 of FIG. 1 according to the embodiments of the present invention. A description will be provided of a method of implanting the implant system 10 into a femoral bone 100 as part of a surgical procedure referred to as the first stage of a two-stage hip replacement revision process. As described below in detail, during the first stage, the implant system 10 having a temporary femoral component along with an antibiotic bone cement will be inserted into the femoral bone where the antibiotic will diffuse into the femoral cavity and help reduce infection in the femoral cavity. Once the infection has been eradicated, as part of the second stage of the two-stage procedure, the implant system 10 is removed and a conventional hip prosthesis can be implanted into the femoral cavity.

As part of the first stage of the procedure, an existing hip replacement (not shown) and infected tissue (not shown) is removed from the femoral cavity in preparation for the implantation of the implant. Conventional femoral cavity preparation techniques can be applied such as application of an antibiotic into the femoral cavity.

Referring to FIGS. 1 and 2, as a further step of the first stage of the procedure, the implant system 10 is implanted into the femoral cavity 19. In one embodiment, at least a portion of the interior space of the mold 14 and 114 can be filled with an antibiotic cement composition 62 before the implant is implanted into the femoral cavity. The implant 10 can be a pre-assembled unit with the mold 14, 114 attached to the femoral component 12. The length of the femoral neck of the femoral component can be adjusted using the adjustment mechanism described above to a proper length prior to the cement curing. Such adjustment is selected to provide a proper fit based on patient medical information previously gathered including medical imaging techniques such as a computed tomography scan, X-ray or intraoperatively and by using other techniques. The bone cement composition 62 can comprise freshly mixed uncured bone cement and an antibiotic. The bone cement can be any bone cement known in the art and can be selected based on the requirements of the particular situation. The antibiotic can be selected based on the particular infection that is present in the femoral cavity. The bone cement composition 62, usually comprises a liquid monomer and a powdered polymeric component, can be prepared using well known techniques in the art such as a mixer device. Once the cement composition is mixed, it is inserted into a chamber of a dispenser tool 105 such as a syringe.

The mold 14, 114 is coupled to the groove 42 of head component 31 and clamped thereon. The construct is then placed in a cavity in the proximal femur. Next, the dispensing end of the dispenser tool 105 is inserted into the injection port 38 of the femoral component 12. The dispenser tool 105 is then actuated so that the bone cement composition 62 is introduced into the interior space of the mold. The interior space of the mold is filled with an amount of cement composition sufficient to secure the femoral component in the mold and expand the mold to provide a snug fit for the implant within the femoral cavity. Alternatively, the implant can be filled prior to insertion, and the cement filled implant 10 is then inserted into at least a portion of the femoral cavity 19 with the exterior surface facing the femoral cavity. As the cement filled implant is inserted into the femoral cavity, the cement composition 62 and the mold 14, 114 are allowed to conform to the shape of the femoral cavity. Once the cement cures, the porous weave forming the mold allows diffusion of antibiotic out of the cement, through the mold wall, and into the femoral cavity. In this manner, the implant of the present application does not require the removal of the mold to allow antibiotic diffusion once the implant has been implanted into the femoral cavity.

In another embodiment, only a portion of the implant system 10 is first inserted into the femoral cavity and then filled with the cement composition 62. In other words, at least a portion of the interior space of the mold is filled with cement composition after the implant is inserted into the femoral cavity. In another embodiment, the femoral component 12 and the mold 14 can be separate units which are assembled during the procedure. That is, first the mold 14, 114 is inserted into the femoral cavity and then attached to the femoral component 12.

Once the implant has been inserted into the femoral cavity, other aspects of the procedure can be performed. For example, the head portion 28 can be attached to head portion and adjusted axially. After the implant has completely implanted into the patient, based on the characteristics of the mold and the antibiotic, the antibiotic can diffuse from the interior space of the mold and to the femoral cavity over a period time and help reduce the infection within the femoral cavity. During this time, the patient is provided with sufficient mobility while recovering from the infection.

Once the temporary implant has been implanted and the infection has been reduced to a particular level, the femoral implant system 10 is removed, as part of the second stage of the procedure. Because of the structure of the implant system 10, removal of the implant is relatively simple. Because no cement contacts bone, mold 14 does not attach itself to the bone surrounding the cavity. In addition, the tapered shape of the mold 14 limits the expansion of the distal region such that it is undersized relative to the surrounding bone thereby facilitating removal of the implant 10 during the second stage. The tapered shape of the mold 14 also allows the proximal region to expand to the shape of the proximal femoral cavity. The diffusion characteristics of the mold wall allow for pressurization of the cement to obtain temporary fixation without having the cement come into contact with the bone.

Once the temporary femoral implant system 10 has been removed, a conventional hip prosthesis (not shown) can be implanted into the femoral cavity 19. The implant system 10 of the present invention provides various advantages. For example, the implant reduces the time for making as well as implanting a temporary implant for a two-stage revision procedure.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A femoral component implant system for use with antibiotic bone cement comprising:
   a flexible mold adapted to fit at least partially in a femoral cavity, the mold having a porous wall with an interior surface and exterior surface, wherein the wall forms an interior space for receiving a bone cement composition comprising uncured bone cement and an antibiotic, wherein the porous wall allows the antibiotic to diffuse from the interior surface and to the exterior surface;
   a femoral component having a stem portion to fit at least partially within the interior space of the mold and a head portion coupled to the stem portion including a portion for contacting and sealing a proximal end of the mold, wherein the femoral component further comprises a head portion with at least a partially spherical shape adapted to fit into an acetabular cavity, and wherein the head portion includes an injection port with an opening extending through the head portion adapted to allow the bone cement composition to be injected into the interior space of the mold.

2. The implant system of claim 1, wherein pores in the wall of the mold allow only the antibiotic to diffuse to the exterior mold surface.

3. The implant system of claim 1, wherein the mold is adapted to substantially inhibit the uncured bone cement from diffusing to the exterior surface.

4. The implant system of claim 1, wherein the exterior mold wall surface is coated with an antibiotic adapted to diffuse away from the exterior surface and into the femoral cavity.

5. The implant system of claim 1, wherein the mold is a generally elongated liner having a distal end and a proximal end, wherein the mold tapers inwardly from the proximal end to the distal end.

6. The implant system of claim 5, wherein the distal end of the mold is adapted to fit into a femoral cavity.

7. The implant system of claim 5, wherein the distal end is closed and the proximal end is open, adapted to receive a bone cement composition.

8. The implant system of claim 1, wherein the distal portion of the stem includes a flexible arm.

9. The implant system of claim 1, wherein the head portion includes a check valve surrounding the port therein to prevent the bone cement composition disposed in the interior space from flowing back out through the injection port.

10. The implant system of claim 1, wherein the head portion includes an attachment mechanism adapted to detachably couple an open end of the mold to the head.

11. The implant system of claim 10, wherein the attachment mechanism includes an adjustment mechanism adapted to allow axial adjustment of a neck length of the femoral component.

12. The implant system of claim 1, wherein the mold is detachably coupled to a head of the femoral component to form a pre-assembled unit.

13. A method of treating a bone infection in a bone cavity, the method comprising:
   providing a bone implant system comprising a flexible porous mold and a bone implant component, the bone implant component includes a stem portion adapted to fit at least partially in an interior space in the mold and a head portion coupled to the stem portion, the head portion including a distal area for contacting and sealing a proximal end of the mold;
   inserting at least a portion of the implant system into the bone cavity with an exterior surface of the mold contacting a femoral cavity;
   sealing the proximal end of the mold to the distal area of the head portion;
   filling at least a portion of the interior space of the mold with an uncured antibiotic bone cement composition through a passageway in the head portion; and
   allowing the antibiotic to diffuse through the porous mold to treat the infection.

14. The method as set forth in claim 13, wherein the interior space of the mold is filled through a port in the bone implant.

15. The method of claim 13, wherein filling the interior space of the mold with the uncured bone cement composition occurs prior to inserting the implant into the bone cavity.

16. The method of claim 13, wherein filling the interior space of the mold with the uncured bone cement composition occurs after inserting the implant into the bone cavity.

17. The method of claim 13, further comprising adjusting a length of the stem portion to provide a proper fit within the bone.

18. The method of claim 13, further comprising removing a hip prosthesis and infected tissue from the bone cavity prior to insertion of the implant system into the bone cavity.

19. The method of claim 13, further comprising allowing the bone cement and a portion of the mold to conform to the shape of the bone cavity prior to curing the bone cement.

20. The method of claim 13, further comprising allowing the antibiotic to diffuse from the exterior surface to the bone cavity to reduce infection in the bone cavity to a sufficient level.

21. The method of claim 13, further comprising removing the implant system from the bone cavity after the antibiotic has diffused into the bone cavity and reduced infection in the bone cavity to a sufficient level.

22. The method of claim 13, further comprising implanting a joint prosthesis into the bone cavity after removing the implant system from the bone cavity.

23. The method of claim 13, wherein the flexible mold is inserted into the bone cavity prior to insertion of the stem portion into the bone cavity.

24. The method of claim 13, wherein the flexible mold is attached to the bone component to form a pre-assembled implant unit prior to inserting the system into the bone cavity.

25. A femoral component implant system for use with antibiotic bone cement comprising:
- a flexible mold adapted to fit at least partially in a femoral cavity, the mold having a porous wall with an interior surface and exterior surface, wherein the wall forms an interior space for receiving a bone cement composition comprising uncured bone cement and an antibiotic, wherein the porous wall is adapted to allow the antibiotic to diffuse from the interior surface and to the exterior surface; and
- a femoral component having a stem portion to fit at least partially within the interior space of the mold and seal a proximal end of the mold wherein the femoral component further comprises a head portion with at least a partially spherical shape adapted to fit into an acetabular cavity wherein the head portion includes an injection port with an opening extending through the head portion adapted to allow the bone cement composition to be injected into the interior space of the mold.

26. A femoral component implant system for use with antibiotic bone cement comprising:
- a flexible mold adapted to fit at least partially in a femoral cavity, the mold having a porous wall with an interior surface and exterior surface, wherein the wall forms an interior space for receiving a bone cement composition comprising uncured bone cement and an antibiotic, wherein the porous wall allows the antibiotic to diffuse from the interior surface and to the exterior surface;
- a femoral component having a stem portion to fit at least partially within the interior space of the mold and a head portion coupled to the stem portion including a portion for contacting and sealing a proximal end of the mold, wherein the femoral component further comprises a head portion with at least a partially spherical shape adapted to fit into an acetabular cavity, and wherein the head portion includes an injection port with an opening extending through the head portion adapted to allow the bone cement composition to be injected into the interior space of the mold;
- wherein the femoral component further comprises a head portion with at least a partially spherical shape adapted to fit into an acetabular cavity;
- wherein the head portion includes an attachment mechanism adapted to detachably couple an open end of the mold to the head; and
- wherein the attachment mechanism includes an adjustment mechanism adapted to allow axial adjustment of a neck length of the femoral component.

* * * * *